US00PP27006P2

(12) United States Plant Patent
Koppe

(10) Patent No.: US PP27,006 P2
(45) Date of Patent: Aug. 2, 2016

(54) *BEGONIA* PLANT NAMED 'KRBARRE04'

(50) Latin Name: *Begonia×hiemalis*
Varietal Denomination: KRBARRE04

(71) Applicant: Lubbertus H. Koppe, Putten (NL)

(72) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 107 days.

(21) Appl. No.: 14/121,544

(22) Filed: Sep. 17, 2014

(51) Int. Cl.
*A01H 5/02* (2006.01)

(52) U.S. Cl.
USPC ..... Plt./349

(58) Field of Classification Search
USPC ..... Plt./349
See application file for complete search history.

(56) References Cited

PUBLICATIONS

UPOV PLUTO: Plant Variety Database, hit on *Begonia* plant named 'KRBARRE04', QZ PBR 39380, published Feb. 15, 2014.*

* cited by examiner

*Primary Examiner* — Anne Grunberg
(74) *Attorney, Agent, or Firm* — C. A. Whealy

(57) ABSTRACT

A new and distinct cultivar of *Begonia* plant named 'KRBARRE04' characterized by its upright, outwardly spreading and mounded plant habit; vigorous growth habit; freely branching habit; dark green-colored leaves; numerous large double bright red-colored flowers that are held above and beyond the foliar plane; and excellent postproduction longevity.

2 Drawing Sheets

Botanical designation: *Begonia×hiemalis.*
Cultivar denomination: 'KRBARRE04'.

BACKGROUND OF THE INVENTION

The present invention relates to a new and distinct cultivar of *Begonia* plant, botanically known as *Begonia×hiemalis*, commercially known as Elatior *Begonia* and hereinafter referred to by the name 'KRBARRE04'.

The new *Begonia* plant is a naturally-occurring whole plant mutation of *Begonia×hiemalis* 'Barkos', disclosed in U.S. Plant Pat. No. 9,523. The new *Begonia* plant was discovered and selected by the Inventor as a single flowering plant from within a population of plants of the parent plant in a controlled greenhouse environment in Ermelo, The Netherlands in March, 2009.

Asexual reproduction of the new *Begonia* plant by vegetative cuttings taken in a controlled greenhouse environment in Ermelo, The Netherlands since March, 2010 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRBARRE04'. These characteristics in combination distinguish 'KRBARRE04' as a new and distinct *Begonia* plant:

1. Upright, outwardly spreading and mounded plant habit.
2. Vigorous growth habit.
3. Freely branching habit.
4. Dark green-colored leaves.
5. Numerous large double bright red-colored flowers that are held above and beyond the foliar plane.
6. Excellent postproduction longevity.

Plants of the new *Begonia* differ primarily from plants of the mutation parent, 'Barkos', in flower size and color as plants of the new *Begonia* have larger and brighter red-colored flowers than plants of 'Barkos'.

Plants of the new *Begonia* can also be compared to plants of *Begonia×hiemalis* 'Balamon', not patented. In side-by-side comparisons conducted in Ermelo, The Netherlands, plants of the new *Begonia* differed primarily from plants of 'Balamon' in flower color as plants of 'Balamon' had orange red-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'KRBARRE04' grown in a container.

The photograph on the second sheet are close up views of the upper and lower surfaces of typical leaves (right) and upper, lateral and lower surfaces of developing and open flowers of 'KRBARRE04' (left).

DETAILED BOTANICAL DESCRIPTION

The aforementioned photographs and following observations and measurements describe plants grown during the spring and early summer in 13-cm containers in a shaded glass-covered greenhouse in Ermelo, The Netherlands and under cultural practices typical of commercial *Begonia* production. During the production of the plants, day temperatures averaged 20° C. and night temperatures averaged 18° C. Plants were pinched one time and were 13 weeks old when the photographs and description were taken. In the following description, color references are made to The Royal Horticultural Society Colour Chart, 2007 Edition, except where general terms of ordinary dictionary significance are used.

Botanical classification: *Begonia×hiemalis* 'KRBARRE04'.

Commercial classification: Elatior *Begonia*.

Parentage: Naturally-occurring whole plant mutation of *Begonia×hiemalis* 'Barkos', disclosed in U.S. Plant Pat. No. 9,523.

Propagation:

*Type*.—By terminal vegetative cuttings.

*Time to initiate roots*.—About 20 days at temperatures about 20° C.

*Time to produce a rooted young plant*.—About five weeks at temperatures about 20° C.

*Root description*.—Fine, fibrous; white to orange brown in color.

*Rooting habit*.—Freely branching; medium density; plants of the new *Begonia* have not been observed to form tubers.

Plant description:

*Plant habit and form*.—Upright, outwardly spreading and mounded plant habit; overall plant shape broadly upright and flattened globular; flowers held above and beyond the foliar plane.

*Growth habit*.—Vigorous growth habit and moderate growth rate; suitable for 12-cm and larger containers; under optimal environmental and cultural conditions, usually about 13 weeks are required to produce proportional 13-cm potted plants from cuttings; vegetative shoots are formed at basal nodes and flowering shoots are formed at upper nodes.

*Branching habit*.—Freely branching habit; when pinched, about seven lateral branches develop.

*Plant height*.—About 28.4 cm.

*Plant width*.—About 41.8 cm.

*Lateral branches*.—Length: About 14.8 cm. Diameter: About 1.5 cm. Internode length: About 3.3 cm. Angle: About 45° from vertical. Texture: Smooth, sparsely pubescent. Color, developing: Close to 152B to 152C. Color, fully developed: Close to 146B to 146C.

*Leaves*.—Arrangement: Alternate; simple. Length: About 14.2 cm. Width: About 16.3 cm. Shape: Reniform to broadly ovate. Apex: Acute. Base: Oblique. Margin: Bi-serrate; laciniate. Texture, upper surface: Smooth, glabrous; velvety. Texture, lower surface: Sparse pubescence along veins. Venation pattern: Palmate. Color: Developing leaves, upper surface: Slightly darker than between N137B and 147A. Developing leaves, lower surface: Between 147B and 148B. Fully expanded leaves, upper surface: Darker than between 139A and 147A; venation, close to 143A to 143B. Fully expanded leaves, lower surface: Close to 191A; venation, close to 146D. Petioles: Length: About 5.9 cm. Diameter: About 8 mm. Texture, upper and lower surfaces: Pubescent. Color, upper surface: Close to 152A to 152B strongly tinged with close to 178A to 178B. Color, lower surface: Close to 152B; distally, close to 178A to 178B. Stipules: Length: About 1.7 cm. Width: About 1.6 cm. Shape: Broadly ovate. Margin: Entire. Texture, upper and lower surfaces: Smooth, glabrous. Color, upper and lower surfaces: Close to 145A tinged with close to 179C.

Flower description:

*Flower form and flowering habit*.—Large double rotate flowers arranged in axillary compound cymes; usually about 8 to 14 flowers per cyme, numerous cymes in flower simultaneously and about 435 flowers developing per plant; flowers face upright to outwardly and are positioned above and beyond the foliar plane.

*Natural flowering season*.—Plants begin flowering about six weeks after pinching; plants flower continuously year round regardless of nyctoperiod, however plants are more freely flowering from spring until autumn in The Netherlands.

*Flower longevity*.—Individual flowers last about ten days on the plant; flowers not persistent; flowering plants have excellent postproduction longevity and typical maintain good substance for about six weeks under interior conditions.

*Fragrance*.—None detected.

*Inflorescence height*.—About 15 cm.

*Inflorescence diameter*.—About 13.7 cm.

*Flower buds*.—Length: About 2.3 cm. Diameter: Ranging from about 8 mm to 19 mm. Shape: Obovate, flattened. Color: Close to 46C to 46D.

*Flowers*.—Shape: Rotate; double. Diameter: About 6.9 cm. Depth (height): About 3.7 cm.

*Tepals*.—Quantity per flower: About four arranged in a single whorl. Length: About 3.8 cm. Width: About 4 cm. Shape: Roughly orbicular. Apex: Rounded. Margin: Entire. Texture, upper surface: Smooth, glabrous; velvety. Texture, lower surface: Smooth, glabrous; slightly velvety. Color: When opening, upper surface: Close to 45B; towards the base, close to 42A. When opening, lower surface: Close to 46A to 46B. Fully opened, upper surface: Close to 45B and 46B; color does not change with development. Fully opened, lower surface: Close to 45B to 45C; towards the base, close to 42B; color does not change with development.

*Tepaloids*.—Quantity per flower: About 5 to 16 arranged in one to several whorls. Length: About 3 cm. Width: About 2.9 cm. Shape: Broadly ovate to orbicular. Apex: Rounded. Margin: Entire to irregularly crenate; slightly undulate. Texture, upper surface: Smooth, glabrous; velvety. Texture, lower surface: Smooth, glabrous; slightly velvety. Color: When opening, upper surface: Close to 45B. When opening, lower surface: Close to 46B. Fully opened, upper surface: Close to 45B; towards the base, close to 43A; color does not change with development. Fully opened, lower surface: Close to 45C; towards the base, close to 43A; color does not change with development.

*Peduncles*.—Length: About 7.7 cm. Diameter: About 8 mm. Angle: About 45° from lateral branch axis. Texture: Sparsely pubescent. Color: Between 148A and 152B.

*Pedicels*.—Length: About 2.3 cm. Diameter: About 3 mm. Angle: About 40° from peduncle axis. Texture: Smooth, glabrous. Color: Close to 175C.

*Reproductive organs*.—Stamens: None observed. Pistils: None observed.

*Seeds and fruits*.—Seed and fruit development have not been observed on plants of the new *Begonia*.

Disease & pest resistance: Resistance to pathogens and pests common to *Begonia* has not been observed on plants of the new *Begonia*.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'KRBARRE04' as illustrated and described.

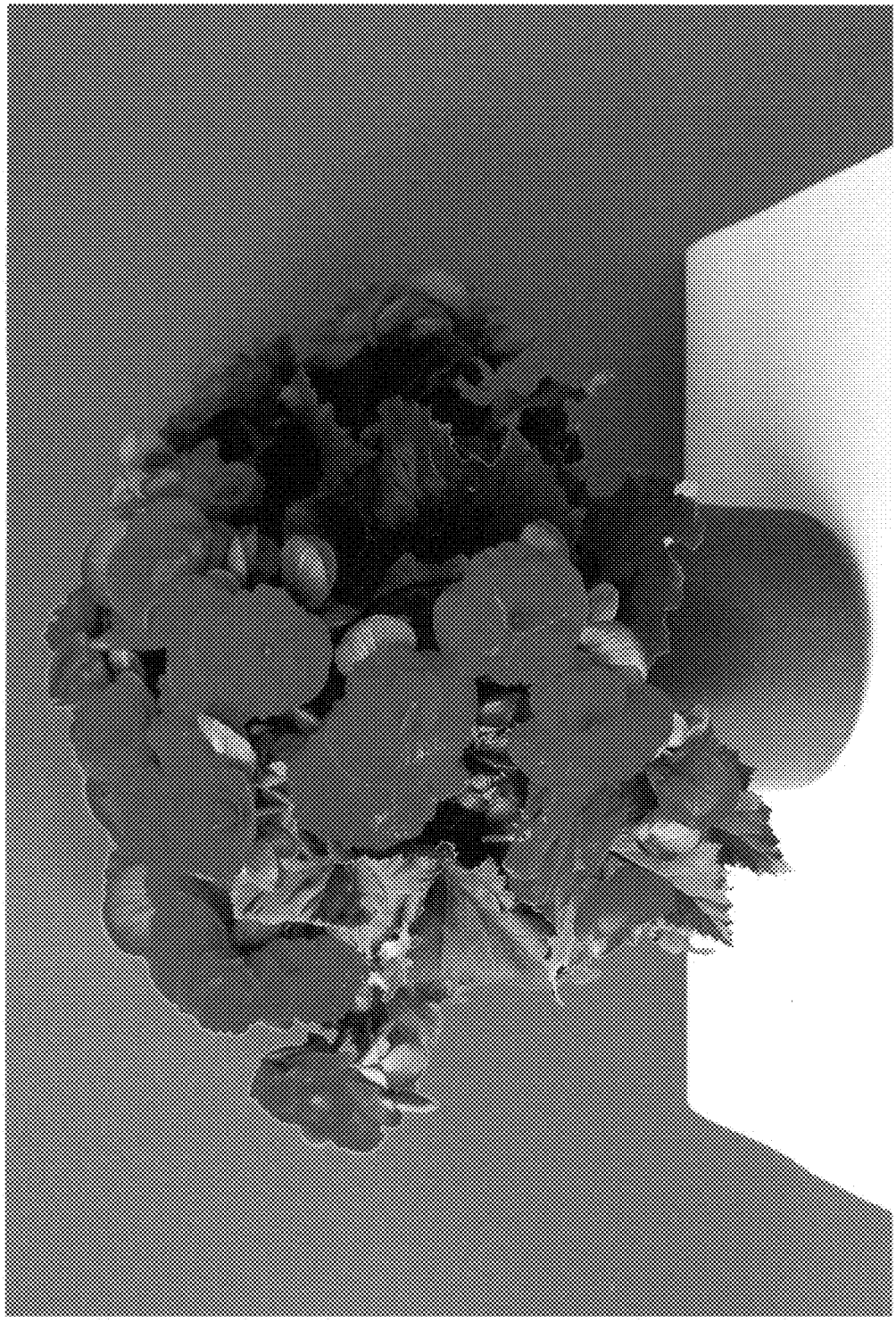

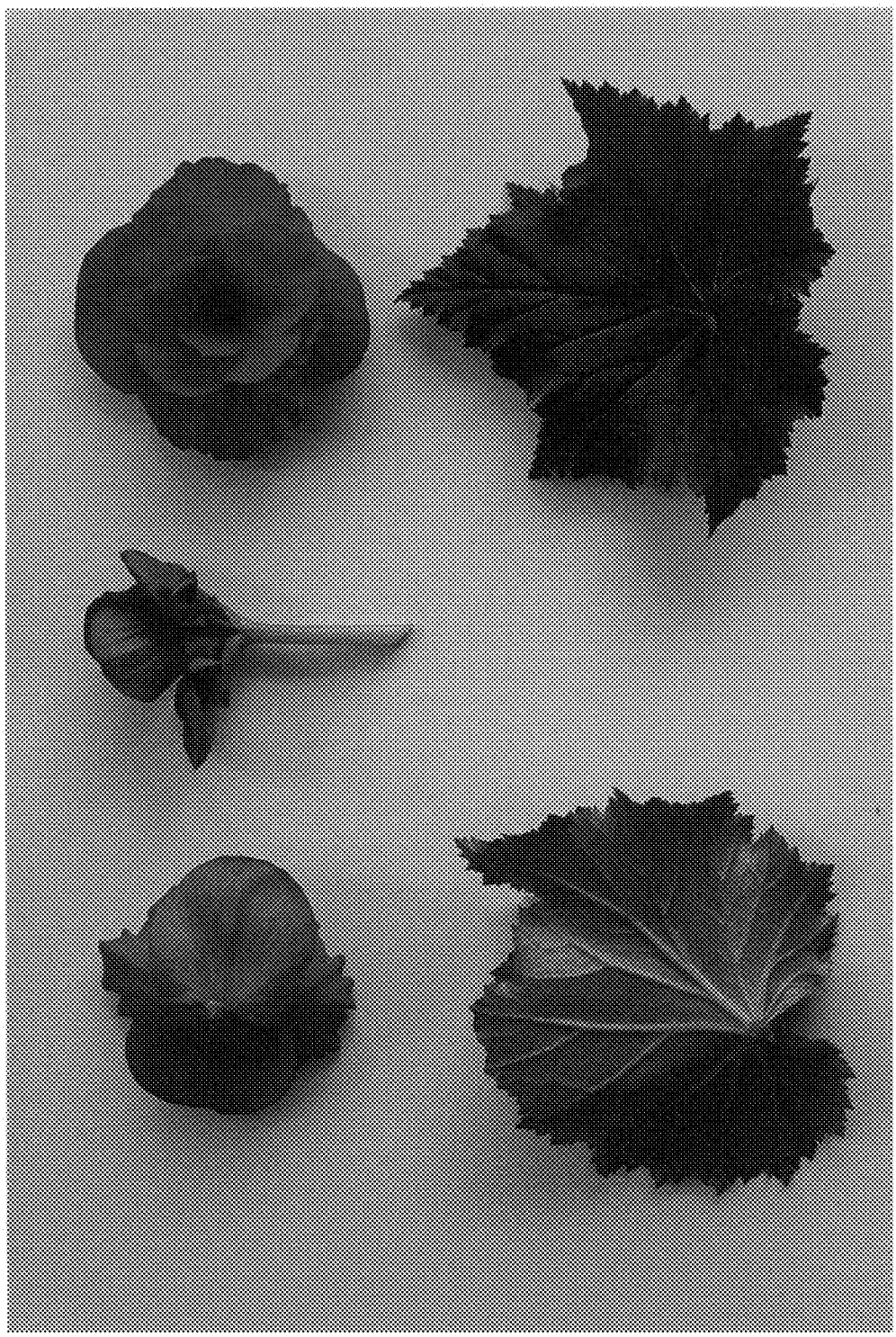

* * * * *